(12) United States Patent
Govari et al.

(10) Patent No.: US 11,717,222 B2
(45) Date of Patent: *Aug. 8, 2023

(54) PROBE DATA MAPPING USING CONTACT INFORMATION

(71) Applicant: BIOSENSE WEBSTER (ISRAEL) LTD., Yokneam (IL)

(72) Inventors: Assaf Govari, Haifa (IL); Andres Claudio Altmann, Haifa (IL); Yaron Ephrath, Karkur (IL)

(73) Assignee: Biosense Webster (Israel) Ltd., Yoknearn (IL)

(*) Notice: Subject to any disclaimer, the term of this patent is extended or adjusted under 35 U.S.C. 154(b) by 0 days.

This patent is subject to a terminal disclaimer.

(21) Appl. No.: 17/850,558

(22) Filed: Jun. 27, 2022

(65) Prior Publication Data

US 2022/0322988 A1 Oct. 13, 2022

Related U.S. Application Data

(63) Continuation of application No. 16/853,210, filed on Apr. 20, 2020, now Pat. No. 11,369,300, which is a continuation of application No. 12/633,324, filed on Dec. 8, 2009, now Pat. No. 10,624,553.

(51) Int. Cl.
| | |
|---|---|
| *A61B 5/283* | (2021.01) |
| *A61B 5/00* | (2006.01) |
| *A61B 5/06* | (2006.01) |
| *A61B 34/20* | (2016.01) |
| *A61B 90/00* | (2016.01) |

(52) U.S. Cl.
CPC .............. *A61B 5/283* (2021.01); *A61B 5/062* (2013.01); *A61B 5/6885* (2013.01); *A61B 90/06* (2016.02); *A61B 34/20* (2016.02); *A61B 2090/065* (2016.02)

(58) Field of Classification Search
None
See application file for complete search history.

(56) References Cited

U.S. PATENT DOCUMENTS

| | | |
|---|---|---|
| 5,391,199 A | 2/1995 | Ben Haim |
| 5,598,848 A | 2/1997 | Swanson et al. |
| 6,016,439 A | 1/2000 | Acker |
| (Continued) | | |

FOREIGN PATENT DOCUMENTS

| | | |
|---|---|---|
| EP | 1 070 480 A2 | 1/2001 |
| EP | 2 075 763 A1 | 7/2009 |
| (Continued) | | |

OTHER PUBLICATIONS

EP Search Report for Application No. EP 10 25 2073, dated Apr. 7, 2011.

*Primary Examiner* — Shahdeep Mohammed

(74) *Attorney, Agent, or Firm* — Lewis Roca Rothgerber Christie LLP

(57) ABSTRACT

A method of mapping includes receiving inputs measured by a probe at respective locations inside a body cavity of a subject. At each of the respective locations, a respective contact quality between the probe and a tissue in the body cavity is measured. The inputs for which the respective contact quality is outside a defined range are rejected, and a map of the body cavity is created using the inputs that are not rejected.

16 Claims, 2 Drawing Sheets

(56) References Cited

U.S. PATENT DOCUMENTS

| | | | |
|---|---|---|---|
| 6,052,618 | A | 4/2000 | Dahlke et al. |
| 6,171,303 | B1 | 1/2001 | Ben-Haim et al. |
| 6,216,027 | B1 | 4/2001 | Willis et al. |
| 6,239,724 | B1 | 5/2001 | Doron et al. |
| 6,298,257 | B1 | 10/2001 | Hall et al. |
| 6,332,089 | B1 | 12/2001 | Acker et al. |
| 6,484,118 | B1 | 11/2002 | Govari |
| 6,618,612 | B1 | 9/2003 | Acker et al. |
| 6,690,963 | B2 | 2/2004 | Ben-Haim et al. |
| 6,915,149 | B2 | 7/2005 | Ben Haim |
| 9,492,226 | B2 * | 11/2016 | Fish ............... A61B 34/73 |
| 2002/0065455 | A1 | 5/2002 | Ben-Haim et al. |
| 2003/0120150 | A1 | 6/2003 | Govari |
| 2004/0068178 | A1 | 4/2004 | Govari |
| 2006/0200049 | A1 | 9/2006 | Giovanni et al. |
| 2006/0253030 | A1 | 11/2006 | Altmann et al. |
| 2006/0286137 | A1 | 12/2006 | Sandhu et al. |
| 2007/0100332 | A1 | 5/2007 | Paul et al. |
| 2007/0276185 | A1 | 11/2007 | Gono et al. |
| 2008/0015568 | A1 | 1/2008 | Paul et al. |
| 2008/0097475 | A1 | 4/2008 | Jaggi et al. |
| 2008/0161668 | A1 | 7/2008 | Wittkampf et al. |
| 2008/0287777 | A1 | 11/2008 | Li et al. |
| 2009/0076476 | A1 | 3/2009 | Barbagli et al. |
| 2009/0093806 | A1 | 4/2009 | Govari et al. |
| 2009/0137952 | A1 | 5/2009 | Ramamurthy et al. |
| 2009/0138007 | A1 | 5/2009 | Govari et al. |
| 2009/0177111 | A1 | 7/2009 | Miller et al. |
| 2009/0208143 | A1 | 8/2009 | Yoon et al. |

FOREIGN PATENT DOCUMENTS

| | | |
|---|---|---|
| EP | 2 248 480 A1 | 11/2010 |
| WO | WO 96/05768 A1 | 2/1996 |
| WO | WO 97/024983 A2 | 7/1997 |
| WO | WO 07/050960 A2 | 5/2007 |

* cited by examiner

PROBE DATA MAPPING USING CONTACT INFORMATION

CROSS REFERENCE TO RELATED APPLICATION

This application is a continuation of U.S. patent application Ser. No. 16/853,210, filed Apr. 20, 2022, now U.S. Pat. No. 11,369,300, which is a continuation of U.S. patent application Ser. No. 12/633,324 filed Dec. 8, 2009, now U.S. patent Ser. No. 10/624,553, the entire content of all of which is incorporated herein by reference.

FIELD OF THE INVENTION

The present invention relates generally to invasive diagnostic techniques, and specifically to mapping of physiological parameters inside the body.

BACKGROUND

A wide range of medical procedures involve placing objects, such as sensors, tubes, catheters, dispensing devices, and implants, within the body. Position sensing systems have been developed for tracking such objects. Magnetic position sensing is one of the methods known in the art. In magnetic position sensing, magnetic field generators are placed below the patient's torso at known positions external to the patient. A magnetic field sensor within the distal end of a probe generates electrical signals in response to these magnetic fields, which are processed in order to determine the position coordinates of the distal end of the probe. These methods and systems are described in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

When placing a probe within the body, it may be desirable to have the distal tip of the probe in direct contact with body tissue. The contact can be verified by measuring either the electrical impedance or the contact pressure between the distal tip and the body tissue. U.S. Patent Application Publications 2007/0100332, to Paul et al., and 2009/0093806, to Govari et al., for example, describe methods of sensing contact pressure between the distal tip of a catheter and tissue in a body cavity using a force sensor embedded in the catheter.

SUMMARY OF THE INVENTION

An embodiment of the present invention provides a method of mapping, which includes receiving inputs measured by a probe at respective locations inside a body cavity of a subject. At each of the respective locations, a respective contact quality between the probe and a tissue in the body cavity is measured. The inputs for which the respective contact quality is outside a defined range are rejected, and a map of the body cavity is created using the inputs that are not rejected.

In a disclosed embodiment, the body cavity includes a chamber of a heart, and receiving the inputs includes receiving signals from a position transducer in the probe that are indicative of coordinates of a distal end of the probe inside the body cavity.

In some embodiments, receiving the inputs includes measuring a physiological parameter at the locations, and creating the map includes mapping the physiological parameter over the cavity. Measuring the physiological parameter may include receiving signals that are indicative of electrical activity in the tissue.

In disclosed embodiments, measuring the respective contact quality includes measuring a pressure exerted on a distal end of the probe. Measuring the pressure typically includes receiving a signal from a force sensor within the probe. Rejecting the inputs may include rejecting measurements when the pressure is below a predetermined lower bound and/or when the pressure is above a predetermined upper bound. In one embodiment, the method includes controlling the probe automatically, responsively to the measured pressure, so as to move the probe within the body cavity.

In an alternative embodiment, measuring the respective contact quality includes measuring an electrical impedance between the probe and the tissue.

In one embodiment, creating the map includes adding tags to the map indicating the respective contact quality at one or more of the locations.

There is also provided, in accordance with an embodiment of the present invention, apparatus for mapping, including a probe, having a distal end configured for insertion into a body cavity and including a contact sensor for measuring a respective contact quality between the probe and a tissue at multiple locations in the body cavity. A console is configured to receive inputs from the probe that are indicative of the contact quality at each of the respective locations, to reject the inputs for which the respective contact quality is outside a defined range, and to create a map of the body cavity using the inputs that are not rejected.

BRIEF DESCRIPTION OF THE DRAWINGS

The disclosure is herein described, by way of example only, with reference to the accompanying drawings, wherein.

DETAILED DESCRIPTION OF EMBODIMENTS

Figure 1:
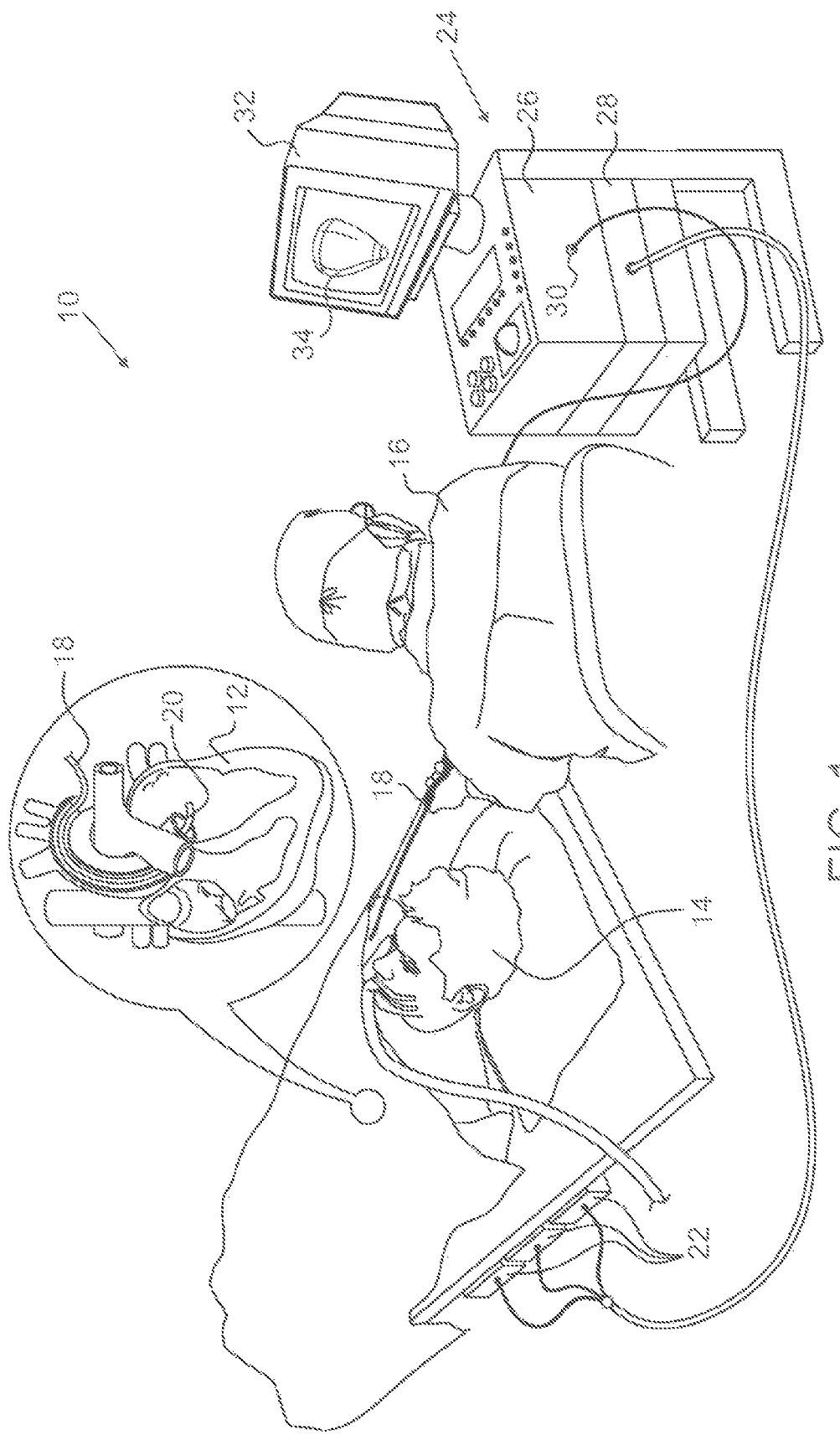
FIG. 1 is a schematic pictorial illustration of a mapping system, in accordance with an embodiment of the present invention.

In electrophysiological diagnostic procedures using an invasive probe, such as intracardiac electrical mapping, it is important to maintain the proper level of force between probe and tissue. Sufficient force is needed in order to ensure good electrode contact between the probe and the tissue. Poor electrical contact can result in inaccurate readings. On the other hand, excessive force can deform the tissue and thus distort the map. In severe cases, too much pressure may cause physical damage to the body cavity wall.

In embodiments of the present invention, acquisition of electrophysiological mapping data (i.e., mapping both probe location and electrical activity in tissue in contact with the probe at the location) is gated so that data points are acquired only when there is adequate contact between the probe and the tissue. The contact quality (i.e., a measure of the adequacy of the contact between the probe and the tissue) may be verified by measuring the contact pressure exerted by the probe against the tissue, using a force sensor as described further hereinbelow. Alternatively, the contact quality may be verified by other means, such as measurement of electrical impedance. Map data points are acquired only when the contact quality is within the desired range. If the contact quality is out of range, the operator may be prompted to reposition the catheter.

In the embodiments that are described hereinbelow, contact gating is used in cardiac electrophysiological mapping. Contact gating limits the collection of map points from the probe to instances in which the contact quality is within a desired range. The term "map point," in the context of the present patent application and in the claims, refers to a set of location coordinates, possibly together with a signal value relating to a physiological parameter at the location of the coordinates. In embodiments that are described below, the signal value that is measured at the map points represents cardiac electrical activity. This sort of contact gating may be useful particularly, for example, in conjunction with techniques such as bipolar electrical mapping and local activation time mapping. Alternatively, contact gating may be used in mapping of other organs, as well as in mapping of other types of physiological parameters. Additionally or alternatively, contact quality information may be added to tags that are associated with data points in the map.

Further alternatively, in some cases the location coordinates may be used to create a map without necessarily recording any other physiological parameter over the map. For example, the tip of a catheter may be moved over the inner surface of a heart chamber (or other body cavity), and data points may be gathered only when the contact pressure is above a certain threshold in order to create a physical map of the surface. Alternatively, the catheter may be moved within the body cavity, and data points may be gathered only when the contact pressure is below a certain threshold in order to create a map of the volume of the cavity. (This volume map may be converted into a surface map by finding and linking the outer points of the volume; various methods may be used for this purpose, such as the ball-pivoting algorithm described in U.S. Pat. No. 6,968,299, whose disclosure is incorporated herein by reference.)

Measuring contact quality can be performed in a variety of ways. In a first embodiment, a force sensor may be embedded in the distal portion of a probe. As the probe comes in contact with body tissue, the pressure of the distal tip of the probe against the tissue is transmitted to a control unit, which will accept mapping data only if the pressure is within a specified range. In an alternative embodiment, a sensor can detect and relay electrical impedance information to the control unit, which will accept the mapping information only if the impedance is within a specified range.

FIG. 1 is an illustration of a position sensing system 10, which is constructed and operative in accordance with a disclosed embodiment of the invention. System 10 may be based, for example, on the CARTO™ system, produced by Biosense Webster Inc. (Diamond Bar, Calif.). System 10 comprises a probe 18, such as a catheter, and a control console 24. In the embodiment described hereinbelow, it is assumed that probe 18 is used in creating electrophysiological maps of one or more heart chambers. Alternatively, probe 18 may be used, mutatis mutandis, for other therapeutic and/or diagnostic purposes in the heart or in other body organs.

An operator 16, such as a cardiologist, inserts probe 18 through the vascular system of a patient 14 so that a distal end 20 of probe 18 enters a chamber of the patient's heart 12. Operator 16 advances probe 18 so that the distal tip of probe 18 engages endocardial tissue at a desired location or locations. Probe 18 is typically connected by a suitable connector at its proximal end to console 24.

Console 24 uses magnetic position sensing to determine position coordinates of distal end 20 inside heart 12. To determine the position coordinates, a driver circuit 28 in console 24 drives field generators 22 to generate magnetic fields within the body of patient 14. Typically, field generators 22 comprise coils, which are placed below the patient's torso at known positions external to patient 14. These coils generate magnetic fields in a predefined working volume that contains heart 12. A magnetic field sensor within distal end 20 of probe 18 (shown in FIG. 2) generates electrical signals in response to these magnetic fields. A signal processor 26 processes these signals in order to determine the position coordinates of distal end 20, typically including both location and orientation coordinates. The method of position sensing described hereinabove is implemented in the above-mentioned CARTO™ system and is described in detail the patents and patent applications cited above.

Processor 26 typically comprises a general-purpose computer, with suitable front end and interface circuits for receiving signals from probe 18 and controlling the other components of console 24. Processor 26 may be programmed in software to carry out the functions that are described herein. The software may be downloaded to console 24 in electronic form, over a network, for example, or it may be provided on tangible media, such as optical, magnetic or electronic memory media. Alternatively, some or all of the functions of processor 26 may be carried out by dedicated or programmable digital hardware components.

An I/O interface 30 enables console 24 to interact with probe 18. Based on the signals received from probe 18 (via interface 30) and other components of system 10, processor 26 drives a display 32 to present operator 16 with a map 34 of cardiac electrophysiological activity, as well as providing visual feedback regarding the position of distal end 20 in the patient's body and status information and guidance regarding the procedure that is in progress. In the present embodiment, processor 26 gates the probe signals, accepting data points for map 34 only when the contact force of distal end 20 against the wall of heart 12 is within a specified range. In some embodiments of the present invention, display 32 provides visual feedback to operator 16 regarding the contact pressure. If the contact pressure is outside the specified range, operator 16 may be prompted to reposition probe 18.

Alternatively or additionally, system 10 may comprise an automated mechanism (not shown) for maneuvering and operating probe 18 within the body of patient 14. Such mechanisms are typically capable of controlling both the longitudinal motion (advance/retract) of probe 18 and transverse motion (deflection/steering) of distal end 20 of probe 18. In such embodiments, processor 26 generates a control input for controlling the motion of probe 18 based on the signals provided by the magnetic field sensor in probe 18. These signals are indicative of both the position of distal end 20 of probe 18 and of force exerted on distal end 20, as explained further hereinbelow. Alternatively or additionally, the measured pressure may be used in automatically controlling the probe within the body. The pressure measurement can be used both in navigating the probe to appropriate mapping locations and to enhance the safety of the procedure by preventing the probe from exerting excessive force on the tissue.

Although FIG. 1 shows a particular system configuration, other system configurations can also be employed to implement embodiments of the present invention, and are thus considered to be within the spirit and scope of this invention.

For example, the methods described hereinbelow may be applied using position transducers of other types, such as impedance-based or ultrasonic position sensors. The term "position transducer" as used herein refers to an element mounted on probe 18 which causes console 24 to receive signals indicative of the coordinates of the element. The position transducer may thus comprise a receiver on the probe, which generates a position signal to the control unit based on energy received by the transducer; or it may comprise a transmitter, emitting energy that is sensed by a receiver external to the probe. Furthermore, the methods described hereinbelow may similarly be applied in mapping and measurement applications using not only catheters, but also probes of other types, both in the heart and in other body organs and regions.

Figure 2:
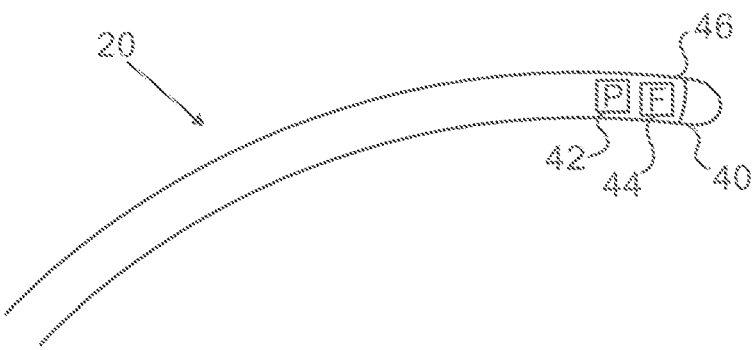
FIG. 2 is a schematic side view showing details of the distal portion of a catheter, in accordance with an embodiment of the present invention.

FIG. 2 is a schematic side view of distal end 20 of probe 18, in accordance with an embodiment of the present invention. Specifically, FIG. 2 shows functional elements of distal end 20 used in creating a map of cardiac electrical activity. An electrode 40 at a distal tip 46 of the probe senses electrical signals in the tissue. Electrode 40 is typically made of a metallic material, such as a platinum/iridium alloy or another suitable material. Alternatively, multiple electrodes (not shown) along the length of the probe may be used for this purpose.

A position sensor 42 generates a signal to console 24 that is indicative of the location coordinates of distal tip 46. Position sensor 42 may comprise one or more miniature coils, and typically comprises multiple coils oriented along different axes. Alternatively, position sensor 42 may comprise either another type of magnetic sensor, an electrode which serves as a position transducer, or position transducers of other types, such as impedance-based or ultrasonic position sensors. Although FIG. 2 shows a probe with a single position sensor, embodiments of the present invention may utilize probes with more than one position sensors.

In an alternative embodiment, the roles of position sensor 42 and magnetic field generators 22 may be reversed. In other words, driver circuit 28 may drive a magnetic field generator in distal end 20 to generate one or more magnetic fields. The coils in generator 22 may be configured to sense the fields and generate signals indicative of the amplitudes of the components of these magnetic fields. Processor 26 receives and processes these signals in order to determine the position coordinates of distal end 20 within heart 12.

A force sensor 44 senses contact between distal tip 46 and endocardial tissue of heart 12, by generating a signal to the console that is indicative of the pressure exerted by distal tip 46 on the tissue. In one embodiment, the force sensor may comprise position sensor 42, together with a magnetic field transmitter and mechanical elements in distal end 20, and may generate an indication of the force based on measuring the deflection of the distal tip. Further details of this sort of probe and force sensor are described in U.S. Patent Application Publications 2009/0093806 and 2009/0138007, whose disclosures are incorporated herein by reference. Alternatively, distal end 20 may comprise another type of contact sensor.

Figure 3:
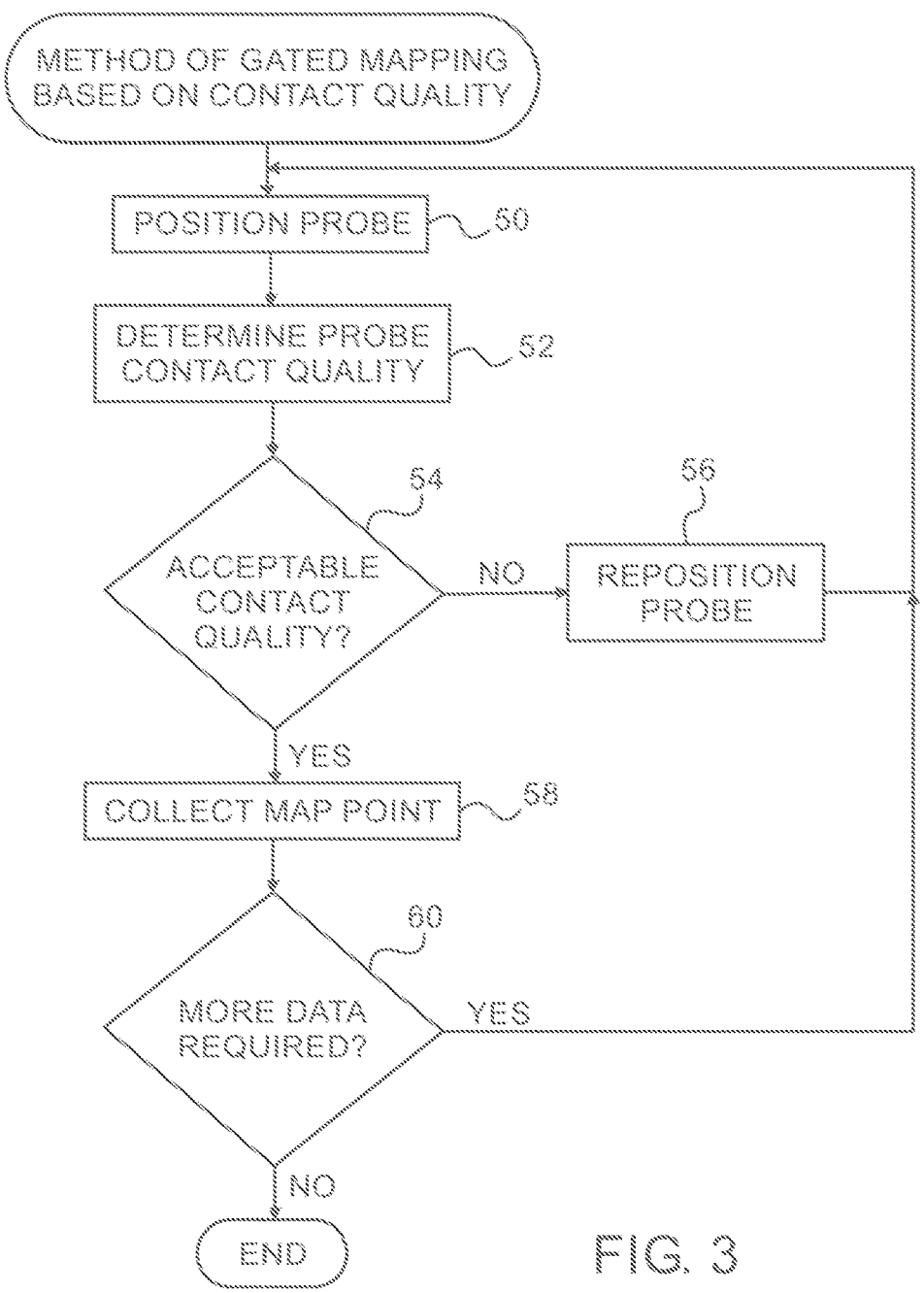
FIG. 3 is a flow diagram that schematically illustrates a method of gated mapping based on contact quality, in accordance with an embodiment of the present invention.

FIG. 3 is a flow diagram that schematically illustrates a method of gated mapping based on contact quality, in accordance with an embodiment of the present invention. After operator 16 positions probe 18 (step 50), processor 26 processes the signals generated by a force sensor 44 in order to derive a measure of contact quality, such as an indication of the pressure exerted by a distal tip 46 of probe 18 on endocardial tissue of heart 12 (step 52). Lower pressure means that there may be inadequate contact between electrode 40 at distal tip 46 and the endocardial tissue. Higher pressure may mean that electrode 40 is pressing too hard against the endocardial tissue. Although the example described here uses pressure to determine contact quality, other methods, such as measuring electrical impedance, can alternatively be used for this purpose.

If the contact quality is not within a specified range (step 54), console 24 outputs an indication to display 32 of the pressure measured using force sensor 44, and may issue an alarm if the pressure is too low or too high, thereby prompting operator 16 to reposition probe 18 (step 56), and the method returns to step 50. For example, when the force exerted by a catheter tip on the heart wall is 5 grams or more, the contact quality may be considered sufficient for mapping, while a force above 35 grams may be dangerously high. Alternatively or additionally, the pressure indication may be used in closed-loop control of an automated mechanism for maneuvering and operating probe 18, as described hereinabove, to ensure that the mechanism causes distal tip 46 of probe 18 to engage the endocardium in the proper location, and with the appropriate pressure against the tissue.

Returning to FIG. 3, if the contact quality is within the specified range (step 54), processor 26 collects a map point, including a coordinate reading from position sensor and an electrical signal from electrode 40 (step 58), and updates map 34. Finally, if operator 16 desires to collect additional mapping data, then the method returns to step 50 until the map is completed.

Although the operation of position sensor 42 and force sensor 44 is described above in the context of using a catheter for acquisition of electrophysiological mapping data, the principles of the present invention may similarly be applied in other therapeutic and diagnostic applications that use invasive probes, both in heart 12 and in other organs of the body. For example, the devices and techniques that are implemented in system 10 may be applied, mutatis mutandis, in gated mapping of other physiological parameters, such as temperature or chemical activity, both in the heart and in other organs. Alternatively or additionally, as mentioned above, contact gating may be used to gather coordinate points (without necessarily measuring other parameters) for use in physical mapping of the surface or volume of a body cavity.

The corresponding structures, materials, acts, and equivalents of all means or steps plus function elements in the claims below are intended to include any structure, material, or act for performing the function in combination with other claimed elements as specifically claimed. The description of the present disclosure has been presented for purposes of illustration and description, but is not intended to be exhaustive or limiting to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

It is intended that the appended claims cover all such features and advantages of the disclosure that fall within the spirit and scope of the present disclosure. As numerous modifications and changes will readily occur to those skilled in the art, it is intended that the disclosure not be limited to the limited number of embodiments described herein. Accordingly, it will be appreciated that all suitable variations, modifications and equivalents may be resorted to, falling within the spirit and scope of the present disclosure.

What is claimed is:

1. A method of mapping a body cavity of a subject using a probe having a distal tip and being operatively connected to a processor, comprising:
   contacting the distal tip of the probe with tissue at a location in the body cavity of the subject causing a deflection of the distal tip, the probe having a distal end configured for insertion into the body cavity of the subject and further comprising a contact force sensor including a position sensor, a first magnetic field transmitter, and a resilient member, the distal end having the distal tip and an electrode, the electrode configured to acquire physiological electrical activity in tissue;
   generating one or more first signals with the position sensor and the first magnetic field transmitter of the contact force sensor indicative of the deflection of the distal tip resulting from a contact pressure exerted on the tissue by the distal tip, and transmitting the one or more first signals to the processor;
   generating one or more second signals with the position sensor and a second magnetic field transmitter, the one or more second signals distinguishable from the one or more first signals and indicative of location and orientation coordinates of the distal end of the probe, and transmitting said one or more second signals to the processor;
   in the processor, measuring the deflection of the distal tip at the location and calculating a respective contact pressure between the probe and the tissue in the body cavity at the location using the one or more first signals;
   rejecting the one or more first signals for which the respective contact pressure is outside a defined range;
   in the processor, automatically collecting a map point only when the calculated respective contact pressure is below a predetermined threshold, the map point including coordinate reading from the position sensor responsive to the second magnetic field transmitter;
   creating or updating a map of a volume of the body cavity using the map point for the one or more first signals that are not rejected; and
   wherein the processor further configured to display the map of the volume of the body cavity.

2. The method according to claim 1, wherein the body cavity comprises a chamber of a heart.

3. The method according to claim 1, wherein rejecting the one or more first signals comprises rejecting the one or more first signals when the respective contact pressure is above a predetermined upper bound.

4. The method according to claim 1, wherein the defined range ranges between 5 and 35 grams.

5. The method of claim 1, further comprising repositioning the probe when the one or more first signals are rejected.

6. The method of claim 1, further comprising providing a visual feedback to reposition the probe when the one or more first signals are rejected.

7. The apparatus of claim 1, further wherein the processor is further configured to provide a visual feedback signal to reposition the probe when the one or more first signals are rejected.

8. The method according to claim 1, further comprising converting the map of the volume into a surface map.

9. The method of claim 8, wherein the converting the map of the volume into the surface map includes finding and linking outer points of the volume.

10. Apparatus for mapping, comprising:
    a probe, having a distal end configured for insertion into a body cavity and further comprising a contact force sensor including a position sensor, a first magnetic field transmitter, and a resilient member, the distal end having a distal tip and an electrode, the electrode being configured to acquire physiological electrical activity in tissue;
    wherein the distal tip of the probe is configured to contact tissue in the body cavity and deflect, the position sensor and the first magnetic field transmitter of the contact force sensor are configured to generate one or more first signals from the position sensor and the first magnetic field transmitter indicative of the deflection of the distal tip resulting from a contact pressure exerted on tissue in the body cavity by the distal tip and transmit said one or more first signals to a console, and the position sensor responsive to a second magnetic field transmitter is configured to generating one or more second signals indicative of location and orientation coordinates of the distal end of the probe and for transmitting said one or more second signals to the console, the one or more second signals distinguishable from the one or more first signals; and
    wherein the console including a processor, which is configured to:
      receive the one or more first signals, the one or more second signals,
      process the one or more second signals for determining the location and orientation coordinates of the distal end of the probe at a location,
      process the one or more first signals to measure the deflection of the distal tip at the location and calculate a respective contact pressure exerted on the tissue by the distal tip,
      automatically reject one or more first signals for which the respective contact pressure is outside a defined range, and
      automatically collect a map point only when the calculated respective contact pressure is below a predetermined threshold, and to create or update a map of a volume of the body cavity using the map point for the one or more first signals that are not rejected, the map point including coordinate reading from the position sensor responsive to the second magnetic field transmitter; and
    wherein the processor is further configured to display the map of the volume of the body cavity.

11. The apparatus according to claim 10, wherein the body cavity comprises a chamber of a heart.

12. The apparatus according to claim 10, wherein the processor is further configured to reject the one or more first signals when the respective contact pressure is above a predetermined upper bound.

13. The apparatus according to claim 10, wherein the defined range ranges between 5 and 35 grams.

14. The apparatus of claim 10, further wherein the processor is further configured to reposition the probe when the one or more first signals are rejected.

15. The apparatus according to claim 10, wherein the processor is further configured to convert the map of the volume into a surface map.

16. The apparatus of claim 15, wherein the processor is further configured to convert the map of the volume into the surface map by finding and linking outer points of the volume.

* * * * *